(12) United States Patent
Kamat et al.

(10) Patent No.: US 8,772,491 B2
(45) Date of Patent: Jul. 8, 2014

(54) PROCESS FOR THE PREPARATION OF SOLIFENACIN SUCCINATE

(75) Inventors: Anand Gopalkrishna Kamat, Hyderabad (IN); Joseph Prabahar Koilpillai, Hyderabad (IN); Naga Trinadhachari Ganala, Hyderabad (IN); Venkata Lakshmi Upputuri, Hyderabad (IN); Venkata Balalji Boddu, Hyderabad (IN); Sivakumaran Meenakshisunderam, Hyderabad (IN)

(73) Assignee: Aurobindo Pharma Ltd, Hyderabad (IN)

( * ) Notice: Subject to any disclaimer, the term of this patent is extended or adjusted under 35 U.S.C. 154(b) by 0 days.

(21) Appl. No.: 13/261,551

(22) PCT Filed: Jun. 20, 2011

(86) PCT No.: PCT/IB2011/001472
§ 371 (c)(1),
(2), (4) Date: Dec. 21, 2012

(87) PCT Pub. No.: WO2012/001481
PCT Pub. Date: Jan. 5, 2012

(65) Prior Publication Data
US 2013/0123502 A1 May 16, 2013

(30) Foreign Application Priority Data

Jun. 28, 2010 (IN) .......................... 1815/CHE/2010

(51) Int. Cl.
*C07D 453/02* (2006.01)

(52) U.S. Cl.
USPC ........................................................ 546/137

(58) Field of Classification Search
None
See application file for complete search history.

(56) References Cited

FOREIGN PATENT DOCUMENTS

EP 1757604 A1 * 2/2007
EP 2088148 A2 * 8/2009

OTHER PUBLICATIONS

International Search Report for PCT/IB2011/001472 dated Oct. 10, 2011.*

* cited by examiner

*Primary Examiner* — Zinna Northington Davis
(74) *Attorney, Agent, or Firm* — Jay R Akhave

(57) ABSTRACT

The present invention relates to a process for the preparation of Solifenacin succinate by condensing a compound of formula (IVb) with (RS)-3-quinuclidinol, wherein, R represents methyl, ethyl, isopropyl; to produce a diastereomeric mixture of (1S)-3,4-dihydro-1-phenyl-2(1H)-isoquinolinecarboxylic acid (3RS)-1-azabicyclo[2.2.2]oct-3-yl ester, which is treated with succinic acid in a solvent or mixture of solvents to produce optically pure Solifenacin succinate, Formula (X).

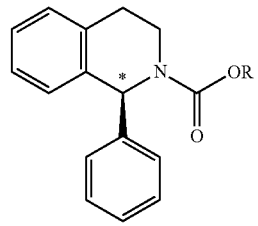

(IVb)

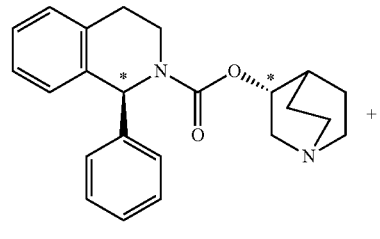

(X)

[(1S,3'R)-isomer]
Solifenacin

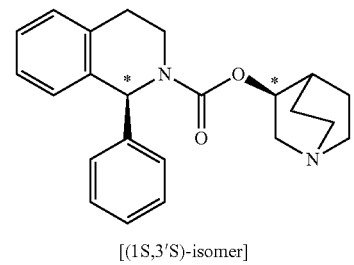

[(1S,3'S)-isomer]
(Diastereomers of Solifenacin)

15 Claims, No Drawings

PROCESS FOR THE PREPARATION OF SOLIFENACIN SUCCINATE

CONTINUING DATA

This application is a 371 application of PCT/IB2011/001472 filed Jun. 20, 2011.

FIELD OF INVENTION

The present invention relates to an improved process for the preparation of Solifenacin succinate of formula (I).

Formula (I)

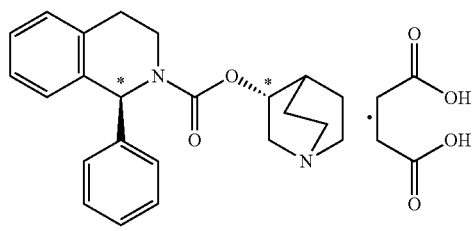

*-represents an asymmetric centre.

BACKGROUND OF THE INVENTION

Solifenacin succinate (I) is chemically known as (1S)-3,4-dihydro-1-phenyl-2(1H)-isoquinoline carboxylic acid (3R)-1-azabicyclo[2.2.2]oct-3-yl ester succinate.

Solifenacin is a potent muscarinic $M_3$ receptor antagonist. Muscarinic receptors play an important role in several major cholinergically mediated functions, including contractions of the urinary bladder, gastrointestinal smooth muscle, saliva production, and iris sphincter function. Solifenacin has greater affinity for the $M_3$ receptor than for the other known muscarinic receptors. Solifenacin succinate is commercially available under the brand name Vesicare®. It has been approved for the treatment of overactive bladder with symptoms of urge urinary incontinence, urgency, and urinary frequency.

Solifenacin (II) and its pharmaceutically acceptable salts are disclosed in U.S. Pat. No. 6,017,927.

According to the process disclosed in U.S. Pat. No. 6,017,927, Solifenacin may be prepared by condensation of (1S)-1-phenyl-1,2,3,4-tetrahydroisoquinoline of formula (III) with ethyl chloroformate to produce (1S)-ethyl 1-phenyl-1,2,3,4-tetrahydro-2-isoquinolinecarboxylate of formula (IV), which is further reacted with (R)-(−)-3-quinuclidinol of formula (V) to produce Solifenacin (II). Solifenacin is converted to Solifenacin hydrochloride by treating with HCl.

Scheme-I

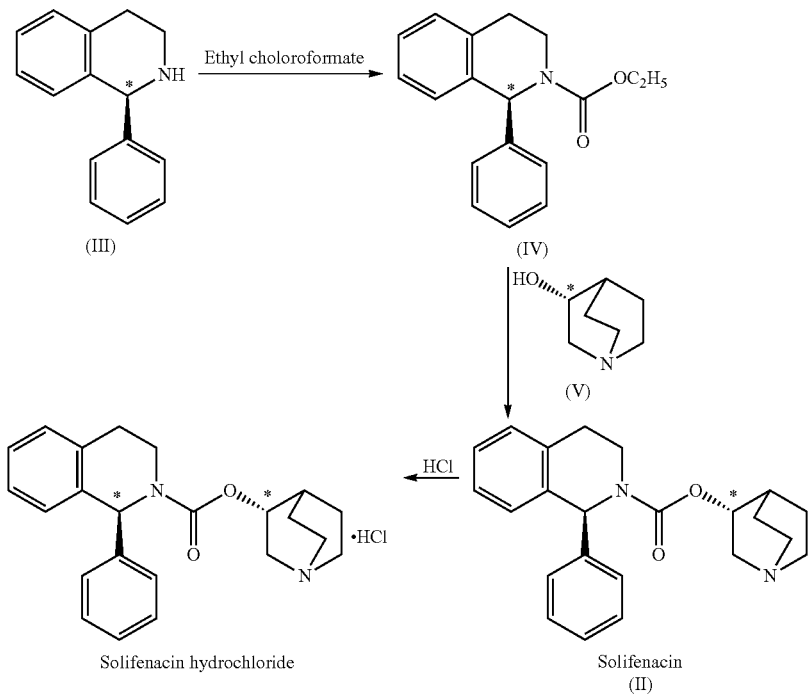

The major disadvantage with the above process is that it involves the use of expensive optically pure R-(−)-3-quinuclidinol. Further, the above process suffers from low yield and low optical purity of Solifenacin.

US '927 also discloses another variant process, wherein (1S)-1-phenyl-1,2,3,4-tetrahydroisoquinoline (III) is reacted with 3-quinuclidinyl chloroformate monohydrochloride (VI) to produce diastereomeric mixture of Solifenacin (IIa) ([(1S,3'R)-isomer] and (1S,3'S)-isomer).

Scheme-II

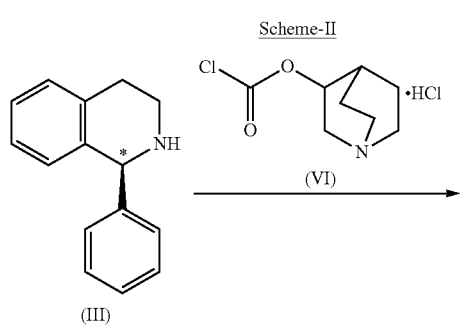

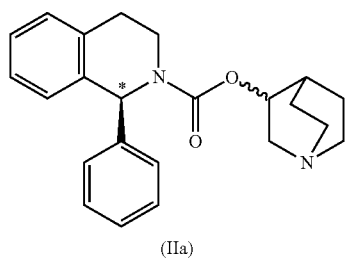

However, the above process is silent about the separation of Solifenacin from the diastereomeric mixture of Solifenacin (IIa) ([(1S,3′R)-isomer] and (1S,3′S)-isomer).

The U.S. Pat. No. 7,829,715 B2 discloses a process for the condensation of racemic ethyl 1-phenyl-1,2,3,4-tetrahydro-2-isoquinolinecarboxylate (IVa) with optically pure (R)-(−)-3-quinuclidinol (V) to produce diastereomeric mixture of Solifenacin (IIb) [(1S,3′R)-isomer and (1R,3′R)-isomer], which is further treated with succinic acid in ethanol and ethyl acetate solvent mixture to produce optically more Solifenacin succinate (I).

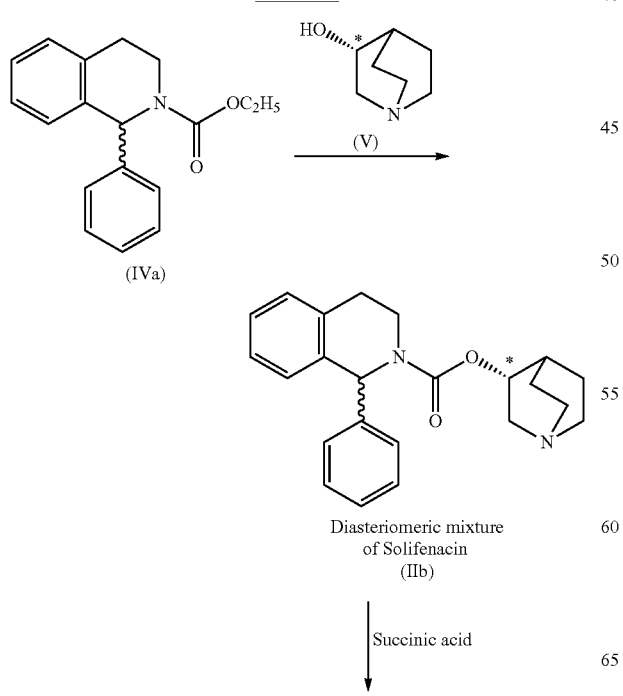

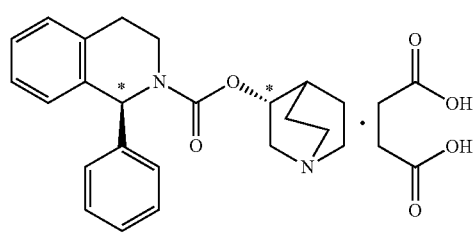

Optically pure Solifenacin succinate
(I)

The above process also involves the use of expensive optically pure R-(−)-3-quinuclidinol. Hence, there is need to provide a simple and cost effective process for Solifenacin succinate. The process of the present invention avoids the use of very expensive optically pure R-(−)-3-quinuclidinol.

The present invention specifically directed towards the process for the preparation of Solifenacin succinate (I), by condensation of (1S)-alkyl 1-phenyl-1,2,3,4-tetrahydro-2-isoquinolinecarboxylate (IVb) with (RS)-3-quinuclidinol (Va) followed by selective isolation of optically pure Solifenacin succinate of formula (I) by diastereomeric crystallization using succinic acid.

OBJECTIVE OF INVENTION

The main objective of the present invention is to provide a simple and effective process for the preparation of Solifenacin succinate of formula (I) on commercial scale.

SUMMARY OF THE INVENTION

Accordingly, the present invention provides a process for the preparation of Solifenacin succinate of formula (I);

Formula (I)

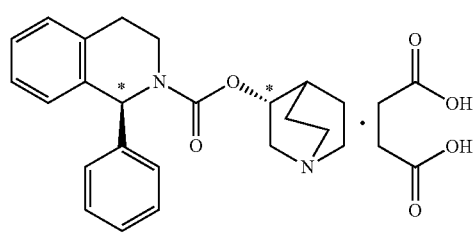

which comprises:
(i) condensing a compound of formula (IVb) with (RS)-3-quinuclidinol of formula (Va), Formula (IVb)

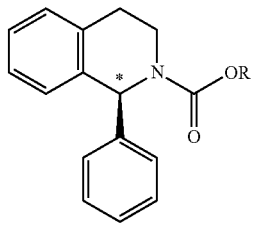

wherein, R represents methyl, ethyl, isopropyl;

Formula (Va)

to produce a diastereomeric mixture of (1S)-3,4-dihydro-1-phenyl-2(1H)-isoquinolinecarboxylic acid (3RS)-1-azabicyclo[2.2.2]oct-3-yl ester,

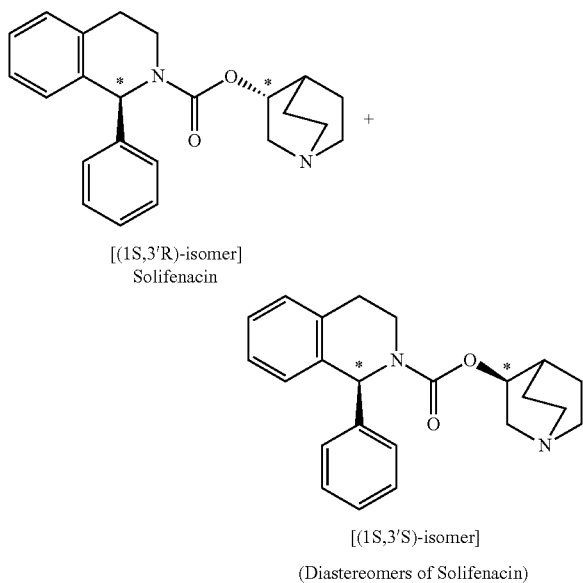 [SMILES: O=C(O[C@H]1CN2CCC1CC2)N1CCc2ccccc2[C@@H]1c1ccccc1 ; O=C(O[C@@H]1CN2CCC1CC2)N1CCc2ccccc2[C@@H]1c1ccccc1]

(Diastereomers of Solifenacin)

(ii) treating the diastereomeric mixture of step (i) with succinic acid in a solvent or mixture of solvents to produce optically pure Solifenacin succinate (I).

In another embodiment, the present invention relates to a single step process for the preparation of Solifenacin succinate without isolating diastereomeric mixture of Solifenacin.

DETAILED DESCRIPTION OF THE INVENTION

The present invention provides a process for the preparation of Solifenacin succinate of formula (I).

The process comprises, (1S)-alkyl 1-phenyl-1,2,3,4-tetrahydro-2-isoquinolinecarboxylate (IVb) is reacted with (RS)-3-quinuclidinol (Va) in the presence of a base in a solvent to produce diastereomeric mixture of (1S)-3,4-dihydro-1-phenyl-2(1H)-isoquinolinecarboxylic acid (3R)-1-azabicyclo[2.2.2]oct-3-yl ester[(1S,3R)-isomer] (Solifenacin base) and (1S)-3,4-dihydro-1-phenyl-2(1H)-isoquinolinecarboxylic acid (3S)-1-azabicyclo[2.2.2]oct-3-yl ester [(1S,3'S)-isomer].

The base used in the reaction is selected from inorganic base such as sodium hydride, potassium hydride, sodium hydroxide, potassium hydroxide, lithium hydroxide, sodium carbonate, potassium carbonate and the organic base such as an amine, for example diethylamine, triethylamine, diisopropylethylamine, tert-butylamine, pyridine. The solvent used in the above reaction is selected from acetonitrile, cyclic or acyclic alkanes such as hexane, heptane, methylcyclohexane, aromatic solvents such as toluene, halogenated solvents such as dichloromethane (MDC), dichloroethane, chloroform, esters such as ethyl acetate, butyl acetate, isopropyl acetate or ethers such as diethyl ether, tetrahydrofuran or tert-butyl methyl ether and/or mixtures thereof. The reaction is carried out at a temperature about 35-100° C. for a period of about 5-36 hours based n solvents used in the reaction. The byproducts formed during the reaction are distilled out by azeotropic distillation. The reaction mass containing Solifenacin and its diastereomer is cooled to about 30-0° C., followed by extracted with a solvent selected from methanol, ethanol, isopropanol, ethyl acetate or mixtures thereof.

The mixture of Solifenacin [(1S,3'R)-isomer and its diastereomer (1S,3'S)-isomer] is treated with succinic acid in a solvent or mixture of solvents to produce crystalline Solifenacin succinate (I).

The crystallization is carried out by heating diastereomeric mixture in a solvent to a temperature from 40° C. to 100° C. and the reaction is stirred for about 3 to 5 hours. The resulting reaction mixture is cooled to 35-0° C. to isolate Solifenacin succinate. The solvent used in the above reaction is selected from methanol, ethanol, isopropanol, ethyl acetate or mixtures thereof.

In another embodiment, the present invention provides an alternative process for the isolation of Solifenacin succinate from diastereomeric mixture.

The process comprises, azeotropic distillation of Solifenacin diastereomeric mixture to remove water, followed by addition of succinic acid and optionally seeded with Solifenacin succinate. The resulting reaction mixture is heated to about 40-100° C. temperature for a period of 1 to 5 hours. The reaction mixture is cooled to 30-0° C. to isolate the Solifenacin succinate.

Solifenacin succinate prepared by above methods is purified by known methods, for example by dissolving in a solvent selected from methanol, ethanol, isopropanol, ethyl acetate or mixtures thereof and precipitating pure Solifenacin succinate (I) by cooling the solution to about 0-30° C., or by adding an anti solvent.

(1S)-Alkyl 1-phenyl-1,2,3,4-tetrahydro-2-isoquinolinecarboxylate (IVb) used in the present invention is prepared by reacting (1S)-1-Phenyl-1,2,3,4-tetrahydroisoquinoline (III) with an alkyl chloroformate in the presence of a base in a solvent.

The alkyl chloroformate used in the above reaction is selected from ethyl chloroformate, methyl chloroformate, isopropyl chloroformate. The solvent used in the above reaction is selected from methylene chloride, 1,2-dichloroethane, toluene and ethyl acetate or mixtures there of. The base used in the above reaction is selected from triethylamine, trimethylamine.

The reaction temperature is about 5-50° C. (1S)-Alkyl 1-phenyl-1,2,3,4-tetrahytho-2-isoquinolinecarboxylate is used as such or by isolating from conventional methods.

The following examples illustrate the nature of the invention and are provided for illustrative purposes only and should not be construed to limit the scope of the invention.

EXAMPLES

Example-1

Stage: 1

Preparation of (1S)-ethyl 1-phenyl-1,2,3,4-tetrahydro-2-isoquinolinecarboxylate

Ethyl chloroformate (5.61 g) was slowly added to a mixture of methylene chloride (100 ml), (1S)-1-phenyl-1,2,3,4-tetrahydroisoquinoline (10 g) and triethylamine (5.32 g) at 5-15° C. over a period of 30 min. Thereafter, the reaction mass was warmed to 25-30° C. and stirred at 25-30° C. for 1 h. The reaction solution was sequentially washed with water (50 ml), 3% w/w hydrochloric acid (50 ml), water (50 ml) and 5% w/w aqueous sodium chloride (50 ml) at 25-30° C. The solvent was removed under reduced pressure at 30-40° C. to produce (1S)-ethyl 1-phenyl-1,2,3,4-tetrahydro-2-isoquinolinecarboxylate (13.0 g) as a pale yellow oil. Chromatographic Purity (By HPLC): 99.22%.

Stage: 2

Preparation of (1S)-3,4-dihydro-1-phenyl-2(1H)-isoquinolinecarboxylic acid (3RS)-1-azabicyclo [2.2.2]oct-3-yl ester[(1S,3'R)- & (1S,3'S)-isomeric mixture] (diastereomeric mixture of Solifenacin)

(RS)-3-Quinuclidinol (7.23 g) was added to a solution of (1S)-ethyl 1-phenyl-1,2,3,4-tetrahydro-2-isoquinolinecarboxylate (10 g) in toluene (50 ml) at 25-30° C. under nitrogen atmosphere. Sodium hydride (60% w/w, 0.27 g) was added to the mixture and the reaction mass was heated to reflux for 24 h. The by-product ethanol was removed azeotropically with toluene and fresh toluene was added to maintain volume of reaction mass. The reaction mass was cooled to 10-15° C. and 10% w/w sodium chloride solution (30 ml) was added slowly at 10-25° C. Then the reaction mass was stirred for about 10 min and toluene layer was separated. The organic layer was then extracted with ~18% w/w aqueous hydrochloric acid (100 ml) at 10-30° C. The aqueous layer was cooled to 5-10° C. and pH was adjusted to 7.0-7.5 using 40% w/w aqueous sodium hydroxide solution (36 ml). Thereafter, the pH was further adjusted to 9.5-10 using 10% w/w aqueous sodium hydroxide solution (11 ml). The product was extracted with ethyl acetate (100 ml) at 25-30° C. Then the organic layer was washed with water (30 ml) and then it was treated with carbon (0.5 g) at 25-30° C. for 30 min. The carbon was removed by filtration through hyflo and the residue was washed with ethyl acetate (20 ml). Thereafter, the filtrate was concentrated under reduced pressure at 40-50° C. to produce 12 g of (1S)-3,4-dihydro-1-phenyl-2(1H)-isoquinolinecarboxylic acid (3RS)-1-azabicyclo[2.2.2]oct-3-yl ester (Solifenacin and its diastereomer) as a pale yellow oil.

Chiral HPLC analysis: Solifenacin: 51.23%; (1S,3'S)-Diastereomer content: 48.65%.

Stage: 3

Preparation of (1S)-3,4-dihydro-1-phenyl-2(1H)-isoquinolinecarboxylic acid (3R)-1-azabicyclo[2.2.2] oct-3-yl ester succinate (Solifenacin succinate)

Solifenacin and its diastereomer (12 g) was dissolved in a mixture of ethanol (12 ml) and ethyl acetate (28 ml) at 25-30° C. Succinic acid (4.2 g) was added and the reaction mass was heated to 60-65° C. and stirred for 1 h. Then the reaction mass was cooled to 25-30° C. and Solifenacin succinate seed crystals were added. Thereafter, the reaction mass was stirred at 25-30° C. overnight. The crystallized product was filtered and was washed with ethyl acetate (10 ml) and then dried under reduced pressure at 50-55° C. to produce of Solifenacin succinate (4.2 g) as white crystals.

Chiral Purity (By HPLC): 96.00%; (1S,3'S)-Diastereomer content: 4.00%.

Above Solifenacin succinate (3.2 g) was suspended in ethyl acetate (48 ml) at 25-30° C. The suspension was heated to 65-70° C. and stirred at 65-70° C. for 2 h. Thereafter, the reaction mass was cooled to 25-30° C. and stirred at 25-30° C. for 1 h. The product was filtered, washed with ethyl acetate (6.4 ml) and then dried under reduced pressure at 50-55° C. to produce Solifenacin succinate—crude (2.88 g).

Chiral Purity (By HPLC): 99.60%; (1S,3'S)-Diastereomer content: 0.40%.

Example-2

Stage: 1

Preparation of (1S)-ethyl 1-phenyl-1,2,3,4-tetrahydro-2-isoquinolinecarboxylate

Ethyl chloroformate (109 g) was slowly added to a mixture of toluene (2000 ml), (1S)-1-phenyl-1,2,3,4-tetrahydroisoquinoline (200 g) and triethylamine (101.50 g) at 5-30° C. over a period of 30 min. Thereafter, the reaction mass was stirred at 25-30° C. for 30 min to complete the reaction. The reaction mass was washed with water (2×600 ml) to obtain toluene solution of (1S)-ethyl 1-phenyl-1,2,3,4-tetrahytho-2-isoquinolinecarboxylate.

Chromatographic Purity (By HPLC): 99.32%.

This solution was taken for condensation reaction with (RS)-3-quinuclidinol in the next stage to prepare Solifenacin and its diastereomer.

Stage: 2

Preparation of (1S)-3,4-dihydro-1-phenyl-2(1H)-isoquinolinecarboxylic acid (3RS)-1-azabicyclo [2.2.2]oct-3-yl ester[(1S,3'R)- & (1S,3'S)-isomeric mixture] (diastereomeric mixture of Solifenacin)

(RS)-3-Quinuclidinol (145.80 g) was added to a solution of (1S)-ethyl 1-phenyl-1,2,3,4-tetrahydro-2-isoquinolinecarboxylate in toluene (as obtained in Stage: 1) at 25-30° C. under nitrogen atmosphere. The contents were heated to 108-112° C. and concentrated to collect ~700 ml of distillate to remove traces of water from the reactants. The contents were cooled to 25-30° C. and sodium hydride (60% w/w, 7.70 g) was added to the mixture and the reaction mass was heated to reflux for about 80 h. The by-product ethanol was removed azeotropically with toluene and fresh toluene was added to maintain volume of reaction mass. The reaction mass was cooled to 20-25° C. and DM water (800 ml) was added slowly at 20-30° C. Then the reaction mass was stirred for about 20 min and toluene layer was separated. DM water (700 ml) was added to the organic layer, cooled to 5-10° C. and pH was adjusted to 1.0±0.2 with ~9% w/w aqueous hydrochloric acid (~350 ml). The aqueous layer was separated, cooled to 5-10° C. and pH was adjusted to 7.0-7.5 using ~10% w/w aqueous sodium hydroxide solution (~170 ml). Thereafter, ethyl acetate (1600 ml) was added and the pH was further adjusted to 10.0±0.2 using ~10% w/w aqueous sodium hydroxide solution (~170 ml). The mass was stirred at 25-30° C. for ~20 min and separated the upper organic layer. The organic layer was washed with DM water (400 ml) and then it was treated with carbon (10 g) at 25-30° C. for 30 min. The carbon was removed by filtration through hyflo and the residue was washed with ethyl acetate (400 ml).

Chiral HPLC analysis: Solifenacin: 51.14%; (1S,3'S)-Diastereomer content: 48.79%.

This solution containing Solifenacin and its diastereomer was taken for diastereomeric crystallization with succinic acid in the next stage to produce Solifenacin succinate.

Stage: 3

Preparation of (1S)-3,4-dihydro-1-phenyl-2(1H)-isoquinolinecarboxylic acid (3R)-1-azabicyclo[2.2.2] oct-3-yl ester.succinate (Solifenacin succinate)

The ethyl acetate solution of Solifenacin and its diastereomer (as obtained in Stage: 2) was dehydrated by azeotropic distillation. To this solution Succinic acid (67.80 g) was added, followed by Solifenacin succinate seed (1 g). The contents were stirred at 25-30° C. for 8 h. Thereafter, the mass was heated to 75-80° C. and stirred at this temperature for 2 h. The slurry was cooled to 25-30° C. and stirred at this temperature for 1 h. The product was filtered and was washed with ethyl acetate (400 ml).

Chiral Purity (By HPLC): 93.69%; (1S,3'S)-Diastereomer content: 6.30%.

Above filtered mass (~250 g) was suspended in ethyl acetate (2000 ml) at 25-30° C. The suspension was heated to 75-80° C. and stirred at this temperature for 2 h. Thereafter, the reaction mass was cooled to 25-30° C. and stirred at this temperature for 1 h. The product was filtered, washed with ethyl acetate (240 ml) and then dried under reduced pressure at 50-55° C. to produce Solifenacin succinate-crude (130 g).

Chiral Purity (By HPLC): 99.44%; (1S,3'S)-Diastereomer content: 0.56%.

Stage: 4

Purification of Solifenacin Succinate

Solifenacin succinate (120 g) as obtained above was stirred in a mixture of ethanol (216 ml) and ethyl acetate (504 ml) at 60-65° C. to obtain a clear solution. This was treated with carbon (6 g) at 60-65° C. for 30 min. Carbon was filtered through hyflo at 60-65° C. and the residue was washed with pre-heated 30% v/v ethanol-ethyl acetate mixture (240 ml). The filtrate was slowly cooled to 0-5° C. and stirred at this temperature for 1 h. Thereafter, the product was filtered, washed with ethyl acetate (120 ml) and then dried under reduced pressure (~20 mm Hg) at 50-55° C. to produce pure Solifenacin succinate (104.50 g).

Chiral Purity (By HPLC): 99.95%; (1S,3'S)-Diastereomer content: 0.05%.

We claim:

1. A process for the preparation of Solifenacin succinate of formula (I);

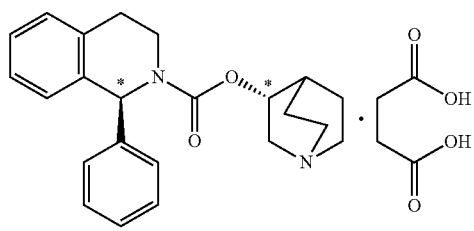

Formula (I)

which comprises:
(i) condensing a compound of formula (IVb) with (RS)-3-quinuclidinol of formula (Va),

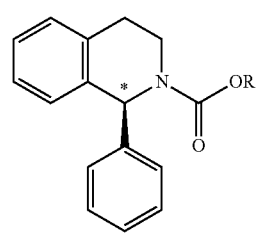

Formula (IVb)

wherein, R represents methyl, ethyl or isopropyl;

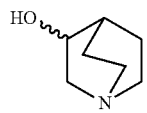

Formula (Va)

to produce a diastereomeric mixture of (1S)-3,4-dihydro-1-phenyl-2(1H)-isoquinolinecarboxylic acid (3RS)-1-azabicyclo[2.2.2]oct-3-yl ester,

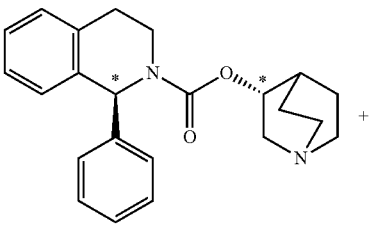

[(1S,3'R)-isomer]
Solifenacin

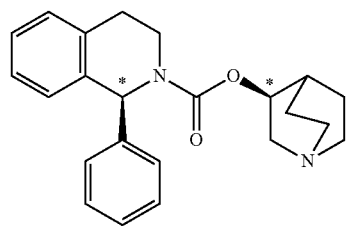

[(1S,3'S)-isomer]
(Diastereomers of Solifenacin)

(ii) treating the diastereomeric mixture of step (i) with succinic acid in a solvent or mixture of solvents to produce optically pure Solifenacin succinate (I).

2. The process according to claim 1, wherein the process of step-(i) is carried out in the presence of a base in a solvent.

3. The process according to claim 2, wherein the said base is inorganic base or organic base.

4. The process according to claim 2, wherein the said solvent used in step-(i) is selected from a group comprising acetonitrile, hexane, heptane, methylcyclohexane, toluene, halogenated solvent ester ether or mixtures thereof.

5. The process according to claim 1, wherein the solvent used in step-(ii) is selected from a croup comprising methanol, ethanol, isopropanol, ethyl acetate, and mixtures thereof.

6. The process according to claim 1, wherein the process is carried out in a single step without isolating diastereomeric mixture of Solifenacin.

7. The process according to claim 1, wherein the compound of formula (IVb) is prepared by a process comprising,
reacting (1S)-1-phenyl-1,2,3,4-tetrahydroisoquinoline of formula (III) with an alkyl chloroformate in the presence of a solvent and a base,

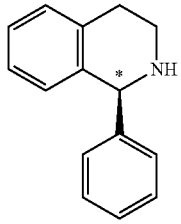

Formula (III)

to produce (1S)-alkyl 1-phenyl-1,2,3,4-tetrahydro-2-isoquinolinecarboxylate of formula (IVb).

8. The process according to claim 7, wherein the alkyl chloroformate is selected from a group comprising ethyl chloroformate, methyl chloroformate and isopropyl chloroformate.

9. The process according to claim 7, wherein the base used is selected from a group comprising triethylamine and trimethylamine.

10. The process according to claim 7, wherein the solvent used is selected from a group comprising methylene chloride, 1,2-dichloroethane; toluene; ethyl acetate, and mixtures thereof.

11. The process according to claim 3, wherein the inorganic base is selected from a group comprising sodium hydride, potassium hydride, sodium hydroxide, potassium hydroxide, lithium hydroxide, sodium carbonate, potassium carbonate, and mixtures thereof.

12. The process according to claim 3, wherein the organic base is selected from a group comprising diethylamine, triethylamine, diisopropylethylamine, tert butylamine, pyridine, and mixtures thereof.

13. The process according to claim 4, wherein the halogenated solvent is selected from a group comprising dichloromethane, dichloroethane, chloroform, and mixtures thereof.

14. The process according to claim 4, wherein the ester is selected from a group comprising ethyl acetate, butyl acetate, isopropyl acetate, and mixtures thereof.

15. The process according to claim 4, wherein the ether is selected from a group comprising diethyl ether, tetrahydrofuran, tert butyl methyl ether, and mixtures thereof.

* * * * *